United States Patent [19]

Murib

[11] 4,205,181

[45] May 27, 1980

[54] PROCESS FOR PREPARING UNSATURATED ESTERS

[75] Inventor: Jawad H. Murib, Cincinnati, Ohio

[73] Assignee: National Distillers and Chemical Corporation, New York, N.Y.

[21] Appl. No.: 972,856

[22] Filed: Dec. 26, 1978

[51] Int. Cl.$^2$ ............................................. C07C 67/05
[52] U.S. Cl. ................................... 560/241; 560/247; 560/246; 260/343.6; 252/467
[58] Field of Search ............... 560/245, 246, 244, 247, 560/241

[56] References Cited

U.S. PATENT DOCUMENTS

| | | | |
|---|---|---|---|
| 3,627,821 | 12/1971 | Sennewald | 560/245 |
| 3,634,496 | 1/1972 | Kominami | 560/245 |
| 3,650,986 | 3/1972 | Sennewald | 560/245 |
| 3,670,014 | 6/1972 | Fernholz | 560/245 |
| 3,922,300 | 11/1975 | Onoda | 560/244 |
| 4,016,200 | 4/1977 | Onoda | 560/245 |
| 4,095,037 | 6/1978 | Stapp | 560/246 |

FOREIGN PATENT DOCUMENTS

| | | | |
|---|---|---|---|
| 45-14528 | 5/1970 | Japan . | |
| 46-9446 | 3/1971 | Japan | 560/245 |
| 47-39006 | 12/1972 | Japan | 560/246 |
| 49-11813 | 1/1974 | Japan | 560/244 |

Primary Examiner—Bernard Helfin
Assistant Examiner—Michael Shippen
Attorney, Agent, or Firm—Kenneth D. Tremain

[57] ABSTRACT

A process for preparing unsaturated esters by oxyacylation which comprises contacting a $C_3$ or higher olefin, oxygen and a carboxylic acid in the vapor phase at an elevated temperature and at a controlled pressure in the presence of a catalytically effective amount of a catalyst comprising an oxide of uranium and at least one oxide selected from the group consisting of arsenic, antimony and bismuth oxides.

8 Claims, No Drawings

PROCESS FOR PREPARING UNSATURATED ESTERS

BACKGROUND OF THE INVENTION

This invention relates to the preparation of unsaturated esters by the catalyzed oxyacylation reaction of $C_3$ or higher olefins, oxygen and a carboxylic acid in the vapor phase.

The preparation of alkenyl esters by the vapor phase reaction of olefins, carboxylic acids and oxygen in the presence of noble metal containing catalysts, especially palladium, is well-known. Thus, when using ethylene, vinyl acetate is obtained, and when using propylene, allyl acetate is prepared. U.S. Pat. No. 3,190,912 granted to Robinson discloses such a reaction and is hereby incorporated by reference.

Over the years, the noble metal catalyzed reaction has been constantly improved because, for one reason, the noble metal catalyst is very expensive and is an important cost factor in the process. In U.S. Pat. No. 3,627,821 the reaction is carried out with a catlyst containing palladium acetate, alkali metal acetate and one or more uranium compounds, said catalyst having improved lifetime and space/time yields. U.S. Pat. No. 3,670,014 uses bismuth in combination with palladium to increase the space/time yields when propylene is the olefin. Lead metal is disclosed as useful in combination with palladium in U.S. Pat. No. 3,917,676 and antimony is used with palladium in U.S. Pat. No. 4,016,200. Improving the process has also resulted in modifications to the palladium containing carrier as shown, for example, in U.S. Pat. No. 3,939,199 wherein the carrier is silicic acid having a special pore volume and pore diameter. It has now been found that $C_3$ or higher olefins may be oxyacylated in the vapor phase to form unsaturated esters without the need for a noble metal catalyst.

It is an object of this invention to provide an improved oxyacylation process for the preparation of unsaturated esters from $C_3$ or higher olefins. Other objects and advantages will become apparent from the following description.

SUMMARY OF THE INVENTION

It has now been discovered that unsaturated esters may be prepared by oxyacylation by contacting a $C_3$ or higher olefin, oxygen and a carboxylic acid in the vapor phase at elevated temperatures and a controlled pressure in the presence of a catalytically effective amount of a catalyst comprising an oxide of uranium and at least one oxide selected from the group consisting of arsenic, antimony and bismuth oxides. A preferred embodiment of the invention is to employ a catalyst comprising an oxide of uranium and an oxide of antimony.

DETAILED DESCRIPTION OF THE INVENTION

The olefins useful in the process of the invention include mono- and diolefins containing from 3 to about 8 carbon atoms and may contain impurities of the type and in amounts normally present in the commercial grades of this reactant. The olefins may contain aromatic, alicyclic or heterocyclic groups and the diolefins may be conjugated or non-conjugated. Among the preferred olefins are those containing from 3 to about 8 carbon atoms, e.g., propylene, butene-1, isobutylene, pentene-1, 3-methyl-butene-1, hexene-1, butadiene, and the like.

The carboxylic acids useful in the invention contain 2 to about 8 carbon atoms, preferably 2 to 6 carbon atoms, with acetic acid being most preferred. Others include, propionic, butyric and the like.

In a highly preferred embodiment of the invention the olefin is propylene and the carboxylic acid is acetic acid, with the valuable product being allyl acetate.

The oxygen may be pure oxygen gas or, alternatively, an oxygen-containing gas mixture such as air or air enriched with oxygen. In addition to these materials the oxygen may contain other inert diluents such as carbon dioxide, nitrogen and the like.

The catalyst herein consists essentially of an oxide of uranium and at least one oxide selected from the group consisting of arsenic, antimony and bismuth. The aforestated oxides can exist in any of their oxidation states and be made from compounds of any oxidation states and specifically include uranium dioxide, uranyl uranate, uranium trioxide, the trioxides, tetroxides and pentoxides of arsenic, antimony and bismuth, and mixtures of these oxides. The atomic ratio of uranium to antimony, bismuth and/or arsenic can vary over wide limits and advantageously is within the ratio of about 50:1 to about 1:99. A ratio of 10:1 to 1:10 is preferred. U.S. Pat. No. 3,198,750 discloses a suitable catalyst containing mixed antimony oxide and uranium oxide and a method for preparing the catalyst, said patent being hereby incorporated by reference.

While it is not necessary to provide the catalysts of this invention with a support, it is generally advantageous to deposit the catalysts upon a carrier such as any of the known and conventional catalyst carrier materials since catalytic efficiency will thereby be significantly improved. Thus, the catalysts herein can advantageously be supported upon silica, alumina, zirconia, silica alumina, silicon carbide, alundum and inorganic silicate in an amount, by weight of metal of the supported catalyst, of about 1 percent to about 90 percent, preferably about 10 to 50 percent. A preferred catalyst contains about 5% to 30% antimony and 1% to 20% uranium, by weight of the supported catalyst.

The catalyst may be prepared by known techniques, e.g., contacting a metal salt solution with the support, drying and calcining in an oxidizing atmosphere, e.g., in the presence of an air sweep. A range of drying temperature of 100°–120° C. and a calcining temperature of 350°–900° C. may be suitably employed. Non-supported catalysts may be prepared by precipitation of the soluble salt or salts from solution by, e.g., neutralization with aqueous ammonia solution, filtration, washing, drying and calcining.

A preferred method for preparing the catalyst comprises treating an extruded or pelletized support with an aqueous solution containing uranyl nitrate and/or antimony pentachloride and concentrated hydrochloric acid. The mixture is evaporated and the impregnated support is dried at 110°–120° C. followed by calcining in air at 450° C. for 12 hours, and at 850° C. for an additional 12 hours. Examples of suitable water soluble metal compounds which can be used in the preparation of the supported catalysts include uranyl nitrate, uranyl chloride, uranyl sulfate, uranyl tetrachloride, arsenic acid, antimony chloride and bismuth nitrate. The catalyst bed can be a fixed bed employing a large particulate or pelleted catalyst or in the alternative, a fluidized bed of catalyst can be utilized.

The catalyst may also contain promoters, such as oxides of molybdenum, thallium, bismuth, copper and silver which are useful, e.g., to improve the selectivity and reaction rate. The amount of promoter, by weight of metal on the supported catalyst, is generally within the range of about 0.1–10%, preferably about 0.5%–3.5%, e.g., 3%.

In general, any apparatus of the type suitable for carrying out reactions in the vapor phase can be used in carrying out the oxyacylation reaction of this invention. The reactor can be brought to the reaction temperature before or after the introduction of the reaction feed mixture. However, in a large-scale operation, it is preferred to carry out the process in a continuous manner and in such a system, the recirculation of unreacted reactants is contemplated.

The concentrations of olefin, carboxylic acid and oxygen used in the oxyacylation reaction can vary widely. The effective minimum concentration of catalyst will depend upon temperature, residence time and the particular composition of the catalyst employed. The mole ratios of oxygen to olefin to carboxylic acid fed to the reaction zone is not critical but is should be adjusted so that the mixture used is not in the explosive region. The stoichiometric ratio of olefin: carboxylic acid: oxygen is 2:2:1 and the relative proportions may vary widely. In general, the olefin may be used in large excess to improve the selectivity to the ester. Broadly stated, in volume percent, based on the total content of olefin, carboxylic acid and oxygen, the oxygen is about 1%–50%, the carboxylic acid is about 1%–77% and the olefin is about 1%–98%. A preferred range is about 1% to 20% oxygen, 2% to 35% carboxylic acid and 45% to 97% olefin. The feed may also be diluted with nitrogen or other inert gas to maintain the mixture outside the explosive limits. Water may be advantageously employed in the reaction and may be present in amounts up to about 25 volume %. The water may be added to the reactor as a separate recycle stream or vaporized recovered unreacted carboxylic acid.

In general, the temperature in the reaction zone is sufficient to maintain the reactants in the vapor state and is about 200°–450° C., preferably about 250°–400° C., although higher or lower temperatures may be employed.

An important feature of the invention is the pressure in the oxyacylation zone. In my copending applications filed concurrently herewith, it is disclosed and claimed that the oxyacylation process is dependent mainly upon the olefin employed and the pressure in the oxyacylation zone. Thus, for example, in the application entitled "Process for Preparing Gamma-Lactones", when alpha-olefins are reacted at low pressure, up to about 40 psig, gamma-lactones are formed, such as gamma-butyrolactone from ethylene. At high pressures, e.g., above about 40 psig, in the application entitled "Process for Preparing Ethylene Glycol Esters", oxyacylation of ethylene produces ethylene glycol esters and, in this application, oxyacylation of $C_3$ or higher olefins, e.g., propylene, produces allyl acetate as a major product. Similarly, oxyacylation of aromatics over a wide range of pressures described in the application entitled "Process for Preparing Aromatic Esters", produces esters, such as benzyl acetate from toluene. In the instant process, it is important to employ a pressure in the oxyacylation zone above about 40 psig, preferably above about 60 psig. Pressures higher than about 1000 psig or higher, may be used but will normally not be employed due to equipment limitations and increased cost. A preferred range is about 60 to 200 psig, with a highly preferred range being about 85 to 110 psig.

The reaction time will depend largely upon the concentration of reactants and therefore, may suitably vary over a wide range. Flow rates are preferably adjusted so that the contact time is in the range of about 0.1 to about 60 seconds, and preferably between about 1 and 5 seconds. The product from the raction may then be recovered by known methods, e.g., extraction, distillation, etc.

The following examples are illustrative of the invention.

EXAMPLE 1

Preparation of the catalyst

Extruded silica gel, 429.5 grams (g.) (⅛ diameter × ¼ long, 200 m²/g surface area) was placed in a 2-liter beaker and treated with 580 ml. aqueous solution containing 284.8 g. $SbCl_5$, 90.6 g. $UO_2(NO_3)_2 \cdot 6H_2O$ and 210 g. concentrated HCl. While mixing, the mixture was heated to dryness on a hot plate. The resulting impregnated extrudates were calcined in air at 450° C. for 12 hours followed by calcining in air at 850° C. for an additional 12 hours.

EXAMPLE 2

Oxyacetylation of Propylene with Acetic Acid and Oxygen at 110 psig and 290° C.

15.1 g of the catalyst prepared in EXAMPLE 1 was packed in a stainless steel reactor (2.5 cm × 12 cm) provided with a thermocouple imbedded in the catalyst bed. The catalyst was heated at 290° C. A gaseous mixture consisting of, by volume, 72.4% propylene, 25.1% glacial acetic acid and 2.5% oxygen was passed through the heated catalyst at a pressure of 110 psig and a contact time of three seconds. The reactor effluent was passed through three traps connected in series; one cooled with ice water and two traps held at dry-ice temperature. The liquid condensates were combined and analyzed for esters and free acetic acid (by alkaline titration and gas chromatography). The vent gases were analyzed by gas chromatography for propylene, oxygen and carbon oxides. The analyses showed that allyl acetate was produced along with small amounts of 1,2-diacetoxypropane, γ-valerolactone and isopropyl acetate.

It will be apparent that many changes and modifications of the several features described herein may be made without departing from the spirit and scope of the invention. It is therefore apparent that the foregoing description is by way of illustration of the invention rather than limitation of the invention.

What is claimed is:

1. A process for the preparation of unsaturated esters which comprises contacting a $C_3$ to $C_8$ olefin, oxygen and a $C_2$ to $C_8$ carboxylic acid in the vapor phase in the presence of a catalytically effective amount of the catalyst consisting essentially of an oxide of uranium and at least one oxide selected from the group consisting of arsenic, antimony and bismuth oxides at an elevated temperature and a pressure above about 40 psig.

2. The process of claim 1 wherein the catalyst is an oxide of uranium and an oxide of antimony.

3. The process of claim 2 wherein the catalyst is supported.

4. The process of claim 3 wherein the temperature is about 200°–450° C.

5. The process of claim 4 wherein the pressure is about 60 to 200 psig.

6. The process of claim 5 wherein the olefin is propylene.

7. The process of claim 6 wherein the carboxylic acid is acetic acid.

8. The process of claim 1 or 7 wherein, in volume percent, the oxygen is about 1%–50%, the carboxylic acid is about 1%–77% and the olefin is about 1%–98%.

* * * * *